United States Patent
Lary

(12) 
(10) Patent No.: US 6,258,108 B1
(45) Date of Patent: Jul. 10, 2001

(54) INCISOR-DILATOR WITH TAPERED BALLOON

(75) Inventor: Banning Gray Lary, Miami, FL (US)

(73) Assignee: InterVentional Technologies, Inc., San Diego, CA (US)

( * ) Notice: Subject to any disclaimer, the term of this patent is extended or adjusted under 35 U.S.C. 154(b) by 0 days.

(21) Appl. No.: 08/953,224

(22) Filed: Oct. 17, 1997

Related U.S. Application Data

(63) Continuation of application No. 08/713,838, filed on Sep. 13, 1996, now abandoned.

(51) Int. Cl.[7] .................................................. A61B 17/32
(52) U.S. Cl. ............................................ 606/159; 606/194
(58) Field of Search ................................... 606/159, 194, 606/170

(56) References Cited

U.S. PATENT DOCUMENTS

| | | |
|---|---|---|
| 4,263,236 | 4/1981 | Briggs et al. . |
| 4,273,128 | 6/1981 | Lary . |
| 4,292,974 | 10/1981 | Fogarty et al. . |
| 4,456,000 * | 6/1984 | Schjeldahl et al. ............... 606/194 X |
| 4,723,549 | 2/1988 | Wholey et al. . |
| 4,784,636 | 11/1988 | Rydell . |
| 4,787,388 | 11/1988 | Hofmann . |
| 5,015,231 | 5/1991 | Keith et al. . |
| 5,042,985 | 8/1991 | Elliott et al. . |
| 5,053,044 * | 10/1991 | Mueller et al. ....................... 606/159 |
| 5,078,725 | 1/1992 | Enderle et al. . |
| 5,116,318 | 5/1992 | Hillstead . |
| 5,196,024 | 3/1993 | Barath . |
| 5,324,255 | 6/1994 | Passafaro et al. . |
| 5,338,298 * | 8/1994 | McIntyre ............................ 606/194 X |
| 5,372,601 * | 12/1994 | Lary ....................................... 606/159 |
| 5,387,225 * | 2/1995 | Euteneuer et al. ..................... 606/194 |
| 5,556,405 | 9/1996 | Lary . |

FOREIGN PATENT DOCUMENTS

| | | |
|---|---|---|
| 0 426 322 A1 | 5/1991 | (EP) . |
| 0 485 903 A2 | 5/1992 | (EP) . |
| 0565796 A1 | 10/1993 | (EP) . |
| 0 623 315 A1 | 11/1994 | (EP) . |
| 0 721 766 A1 | 7/1996 | (EP) . |
| 1516120 | 10/1989 | (SU) . |
| WO 90/07909 | 7/1990 | (WO) . |

OTHER PUBLICATIONS

Banning G. Lary, MD, *Coronary Artery Incision and Dilation*, pp. 1478–1480, Arch Surg, vol. 115, Dec. 1980.

* cited by examiner

Primary Examiner—Michael H. Thaler
(74) Attorney, Agent, or Firm—Nydegger & Associates

(57) ABSTRACT

The present invention is a device for incision and dilation of stenotic segments within the vascular system of a patient. Structurally, the present invention includes a rigid ellipsoidal dilation probe mounted at the distal end of a catheter. A series of longitudinally oriented blades project radially from the surface of the probe. A tapered inflatable balloon is also mounted on the catheter in a position that is proximal to the dilation probe. In use, the probe and catheter are advanced over a guidewire to reach the targeted stenotic segment. The probe and blades are then advanced through the stenotic segment to incise the stenosis. The balloon may then be inflated to adopt a tapering fusiform shape, allowing the balloon to be advanced through the stenosis to further dilate the stenosis. Alternatively, the balloon may be positioned across the stenosis and inflated to dilate the stenosis. The fusiform shape of the balloon matches the tapering geometry of many coronary arterial vessels, decreasing the chances that a segment of the vessel will be overpressurized by the inflating balloon.

18 Claims, 3 Drawing Sheets

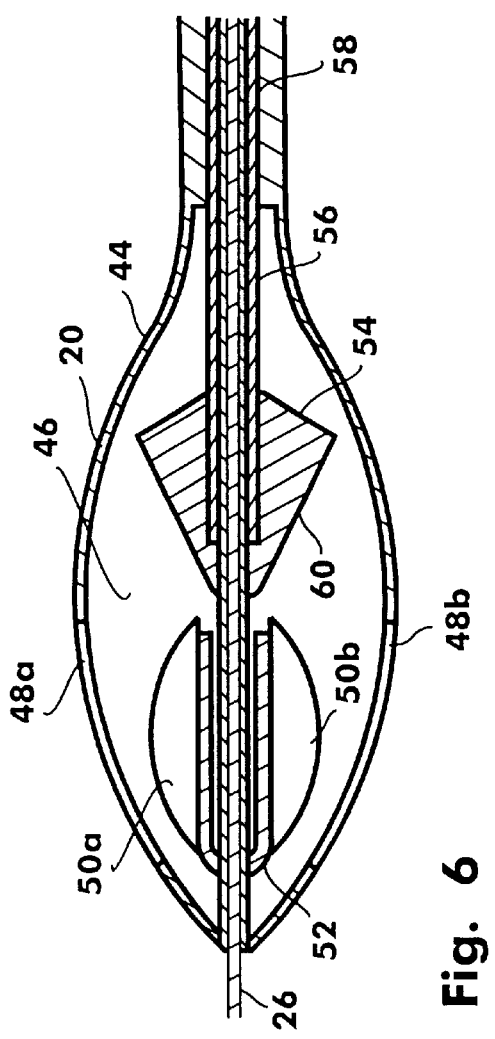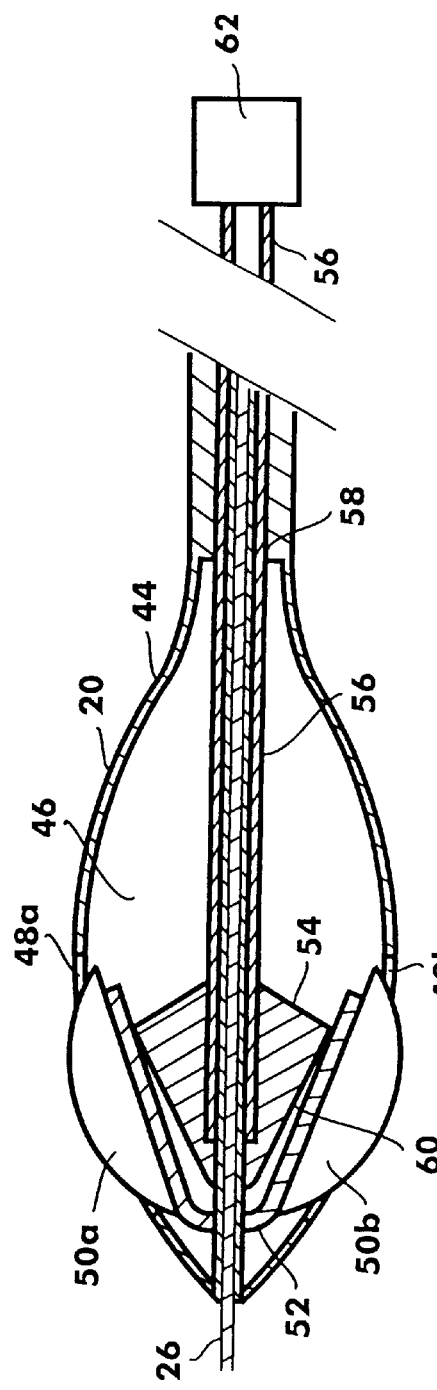

US 6,258,108 B1

INCISOR-DILATOR WITH TAPERED BALLOON

This application is a continuation of Ser. No. 08/713,838 filed Sep. 13, 1996, abandoned.

FIELD OF THE INVENTION

The present invention pertain generally to surgical devices and procedures. More particularly, the present invention pertains to devices and methods for clearing a stenosis from the artery of a patient. The present invention is particularly, but not exclusively useful, for both incising and subsequently dilating a vessel to clear an obstruction or stenosis from the vessel.

BACKGROUND OF THE INVENTION

Many medical complications are created by the total or even partial blockage of blood vessels of the body. The primary cause of these complications is, of course, the reduction or cessation of blood flow through the blocked vessels to the particular biological tissue which is serviced by the vessel. Most commonly, a blockage, or stenosis, is formed in an artery as a result of plaque build-up in the artery. Further, it is not uncommon for several stenoses to occur sequentially in a single artery or to develop near one another in branches of a common central artery.

Several methods, or procedures, have been developed in the medical field for the purpose of removing or clearing stenoses from the vessels of patients. One well known procedure for accomplishing this is an angioplasty procedure such as is disclosed in U.S. Pat. No. Re. 33,561 which issued to Levy for an invention entitled "BALLOON AND MANUFACTURE THEREOF." Basically, in an angioplasty procedure, a deflated dilatation balloon is inserted into the vessel and is placed across the stenosis. Once the balloon is properly positioned, it is inflated to dilate the artery and thereby clear the stenosis. Another, more recently developed procedure for clearing a stenosis, is an atherectomy procedure.

The essential aspects of an atherectomy procedure are set forth in U.S. Pat. No. 4,895,166 which issued to Farr et al. for an invention entitled "ROTATABLE CUTTER FOR THE LUMEN OF A BLOOD VESSEL" and which is assigned to the same assignee as the present invention. As disclosed by Farr et al., in an atherectomy procedure, the stenotic material is actually cut and removed from the artery.

Both the angioplasty procedure and the atherectomy procedure are typically accomplished indirectly wherein access to the stenosis is achieved through a peripheral artery. These procedures are in contrast to other known procedures used to clear arteries, such as a by-pass surgery, where direct access to the stenosis is achieved by entering the artery at or near the site of the stenosis. Despite their differences, the ultimate objective of all these procedures is to remove or alleviate the stenosis which is restricting blood flow through the artery.

Recent studies have indicated that for procedures wherein a stenosis is to be dilated, such as for an angioplasty procedure, the efficacy of the dilatation is enhanced by first incising the material which is creating the stenosis. With this knowledge, several devices for clearing blocked arteries have been proposed. For example, U.S. Pat. No. 4,273,130 which issued to Lary for an invention entitled "CORONARY CUTTING AND DILATING INSTRUMENT" discloses a surgical instrument which both incises and dilates a stenosis. As another example, U.S. Pat. No. 5,209,799 which issued to Vigil for an invention entitled "METHOD FOR MANUFACTURING A FOLDING BALLOON CATHETER" discloses a folding angioplasty balloon with attached cutting blades.

Angioplasty, atherectomy and by-pass surgery procedures, as discussed above, have all been found to be effective procedures for dilation and removal of occluding stenoses. In some cases, however, these procedures have been found to be less effective. For example, it happens that the coronary arteries where many stenoses occur have a tapering geometry with the arteries generally having an internal diameter which is greatest near the heart and which decreases at distances farther from the heart. When a stenosis accumulates in a tapering artery, such as a coronary artery, the stenosis will itself have a tapering geometry. If the stenosis is relatively long, the tapering effect can be quite pronounced. As a result, many of the traditional methods of angioplasty and atherectomy devices may be ineffective, or even harmful. For example, if a traditional angioplasty device is used in a long stenotic segment in a tapering artery, it may over dilate the narrowest part of the stenosis while under dilating the widest part of the stenosis. As a result, the procedure fails to fully clear the stenosis and, possibly, weakens the involved vessel. Similarly, if an incising or atherectomy procedure is to be used in a long stenotic segment in a tapering artery, the cutting diameter of the device will necessarily have to be chosen to protect the narrowest part of the involved vessel, lessening the effectiveness of the procedure on the vessel's widest part.

Even in cases where the stenotic segments are relatively short, the tapering geometry of many vessels may be problematic if a sequence of such segments must be cleared. More specifically, it may be appreciated that where sequences of stenotic segments are involved, and the segments are positioned within a single tapering vessel, treatment may be problematic if the apparatus employed cannot adapt to the decreasing internal diameter of each subsequent stenotic segment.

In light of the above, it is an object of the present invention to provide a device and method for incising and dilating a stenosis in a vessel of a patient which is particularly efficacious for removal of relatively long stenotic blockages in tapering vessels. Another object of the present invention is to provide a device for incising and dilating a stenosis in a vessel of a patient which can be reconfigured in-situ to allow treatment of a sequence of stenotic segments, each positioned further into a tapered vessel. Yet another object of the present invention is to provide a device for incising and dilating a stenosis in a vessel of a patient which is relatively simple to manufacture, is easy to use, and is comparatively cost effective.

SUMMARY OF THE PREFERRED EMBODIMENTS

The present invention is a device and method for incising and dilating stenotic segments within the vessels of a patient which is particularly suitable for use in tapering or narrowing vessels. Structurally, the present invention includes a tubular catheter having a distal end and a proximal end. The catheter is formed to surround an inflation lumen and a guidewire lumen, both of which pass between the catheter's distal and proximal ends.

A rigid probe is mounted at the distal end of the catheter. The probe is preferably formed to taper, or narrow, in the distal direction, giving the probe an overall conical shape. A series of blades are mounted on the surface of the probe, and are positioned to project radially from the surface of the probe. The blades are aligned to extend radially from the longitudinal axis of the catheter and probe.

An inflatable balloon is mounted over the catheter near the catheter's distal end and is positioned to be proximal to the probe and blades. The balloon has a distal end and a proximal end and is attached in fluid communication with the inflation lumen of the catheter. The attachment between the inflation lumen of the catheter and the balloon allows fluid to be passed through the inflation lumen to inflate the balloon. Inflation of the balloon moves the balloon from a first configuration wherein the balloon is deflated and lies along the surface of the catheter to a second configuration wherein the balloon is inflated and has a substantially fusiform shape. In the second configuration, the balloon tapers, with differing gradients, towards both the balloon's distal and proximal ends. Preferably, the fusiform shape of the inflated balloon is biased to give the distal end of the balloon a taper which is more gradual than the taper at the proximal end of the balloon.

In the operation of the present invention, a guidewire is first advanced into the vessel or artery of the patient which requires treatment. The guidewire is advanced until the distal end of the guidewire is positioned within or beyond the stenotic vascular segment that is targeted by the procedure. The proximal end of the guidewire is then threaded through the guidewire lumen of the catheter starting at the catheter's distal end.

The catheter, with the probe, blades and balloon attached, is then advanced over the guidewire and into the vessel of the patient. The advancement of the catheter continues until the probe and blades are positioned to be adjacent to the stenotic segment that is targeted by the procedure. With the probe and blades properly positioned, the probe is advanced through the stenotic segment with the blades incising the segment. The probe may then be reciprocally withdrawn and readvanced to further incise the stenosis.

Once the stenosis has been incised by the blades of the probe, the balloon is positioned across the stenosis and inflated to dilate the stenotic segment. As the balloon inflates, the tapered shape of the balloon mimics the tapered geometry of the surrounding artery. In this way, the balloon is able to provide an expansive force which is evenly distributed over the stenotic segment, reducing the probability of vascular damage due to overexpansion of a particular portion of the vascular wall.

For another mode of operation, the balloon is inflated to become a tapered dilation probe which many be advanced into the stenosis for dilation thereof. The balloon may then be repeatedly advanced and withdrawn until the stenosis has been adequately dilated. Concurrently, the inflation of the balloon may be selectively increased or decreased to further facilitate dilation of the stenotic segment.

For an alternative embodiment of the present invention, the dilation probe and blades of the present invention are modified to allow the blades to be retracted into the dilation probe when not in use. Generally, to enable this type of functionality, the probe of the present invention will be formed as a hollow shell surrounding a chamber. The blades are positioned within the chamber and aligned with a series of slots formed in the surface of the probe. A piston is included within the chamber and positioned to reciprocate, or move translationally within the chamber, in line with the longitudinal axis of the catheter. The piston is connected to a push-pull wire which passes through the catheter. Functionally, advancement of the push-pull wire moves the piston within the chamber. The advancing piston forces each of the blades to project from one of the slots formed in the surface of the probe. In this fashion, the blades may be extended a variable distance from the probe or retracted into the probe.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 6 is a cross-sectional view of an alternate embodiment for the probe of the present invention, as would be seen along the line 6—6 in FIG. 3, shown with the cutting blades positioned in a retracted configuration; and FIG. 7 is a cross-sectional view of an alternate embodiment for the probe of the present invention, as shown in FIG. 6, with the cutting blades positioned in an extended configuration.

DESCRIPTION OF THE PREFERRED EMBODIMENT

Figure 1:
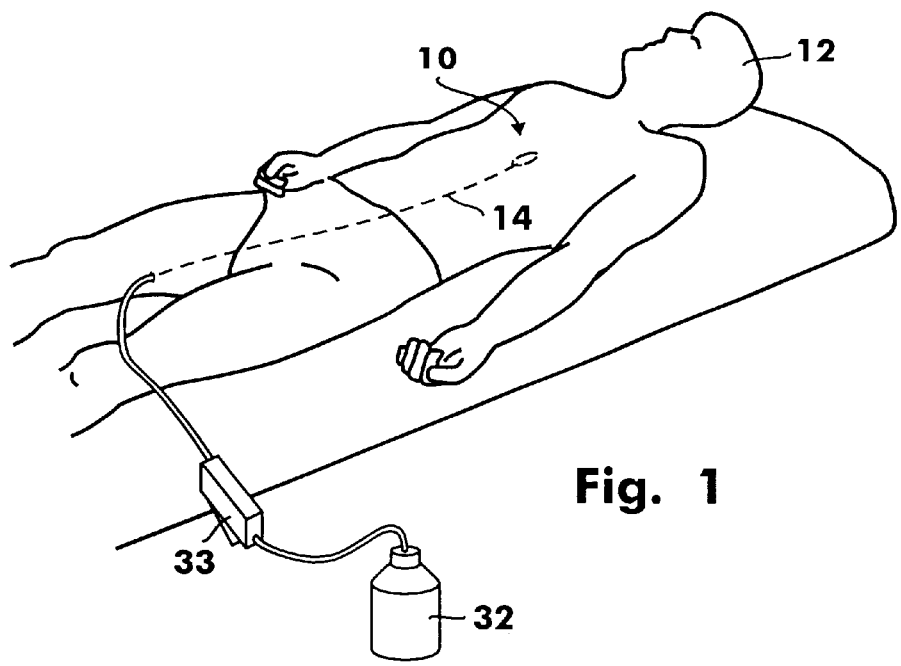
FIG. 1 is a pictorial view of the present invention shown operationally positioned within the vessel of a patient.

Referring initially to FIG. 1, a device for incising and dilating a stenosis within a vessel is shown and generally designated 10. More specifically, the device 10 is shown positioned in the artery of a patient 12. As will be appreciated by the skilled artisan, the device 10 is shown schematically positioned in the patient 12, and it is to be understood that use of the device 10 is not confined to only upper body arteries and vessels but, instead, can be used in arteries and vessels throughout the patient 12.

Figure 2:
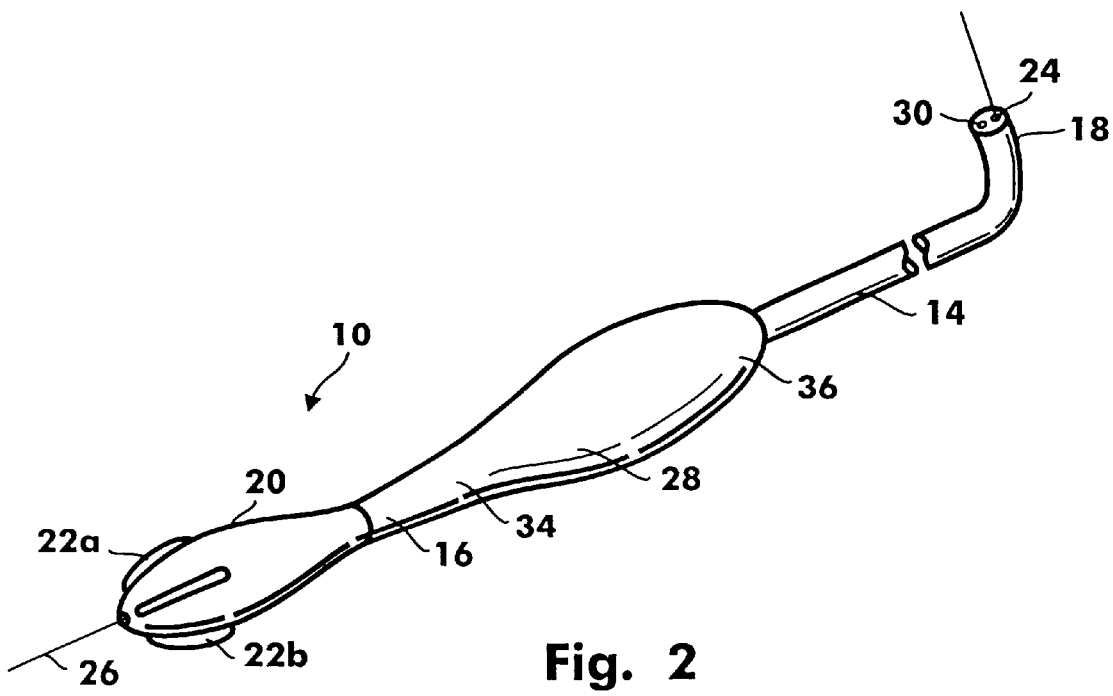
FIG. 2 is a perspective view of the present invention.

The present invention may be better appreciated by reference to FIG. 2 where it may be seen that the device 10 includes a catheter 14 having a distal end 16 and a proximal end 18. A rigid probe 20 having a substantially conical or ellipsoidal shape is mounted at the distal end 16 of the catheter 14. A series of blades 22, of which blades 22a and 22b are representative, project radially from the surface of the probe 20. Each blade 22 is aligned to project radially from the longitudinal axis of the catheter 14. Both the probe 20 and the catheter 14 are formed to surround a guidewire lumen 24. The guidewire lumen 24 passes through the probe 20 and extends between the distal end 16 and the proximal end 18 of the catheter 14. The guidewire lumen 24 allows the probe 20 and catheter 14 to be passed over a guidewire, such as guidewire 26.

Preferably, the device 10 can partly or entirely include a low friction, heparin surface to reduce trauma to the vessel and to slow clotting or coagulating of the blood. A suitable surface treatment can be provided by the company BSI of Eden Prairie, Minn.

The present invention also includes a tapering balloon 28. The balloon 28 is mounted over the catheter 14, near the distal end 16 of the catheter 14, and positioned to be proximal to the probe 20. The balloon 28 is formed from a polymeric material, such as PET and is attached in fluid communication with an inflation lumen 30 formed in the catheter 14. A fluid pressure source 32 and a controller are connected to the proximal end 18 of the catheter 14 and connected in fluid communication with the inflation lumen 30. Functionally, the combination of the balloon 28, inflation lumen 30, fluid pressure source 32 and controller 33 allows the balloon 28 to be filed with a fluid to expand, or inflate, the balloon 28.

Figure 3:
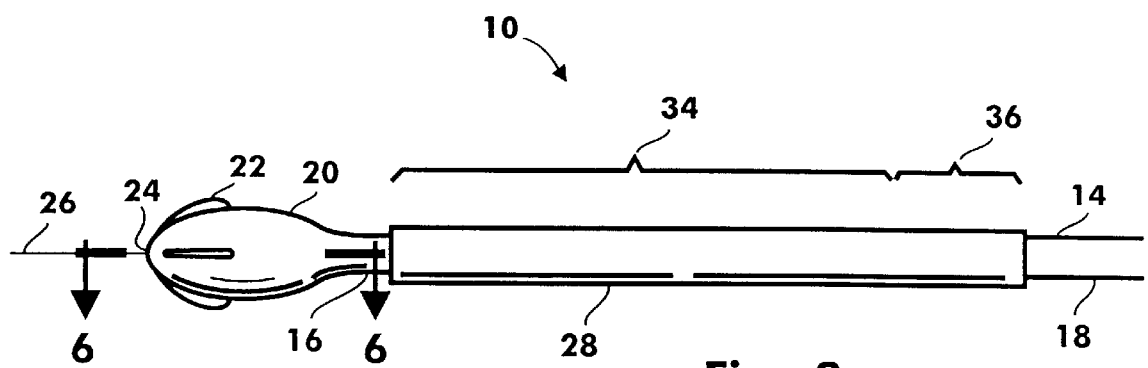
FIG. 3 is a side view of the distal portion of the present invention.
Figure 4:
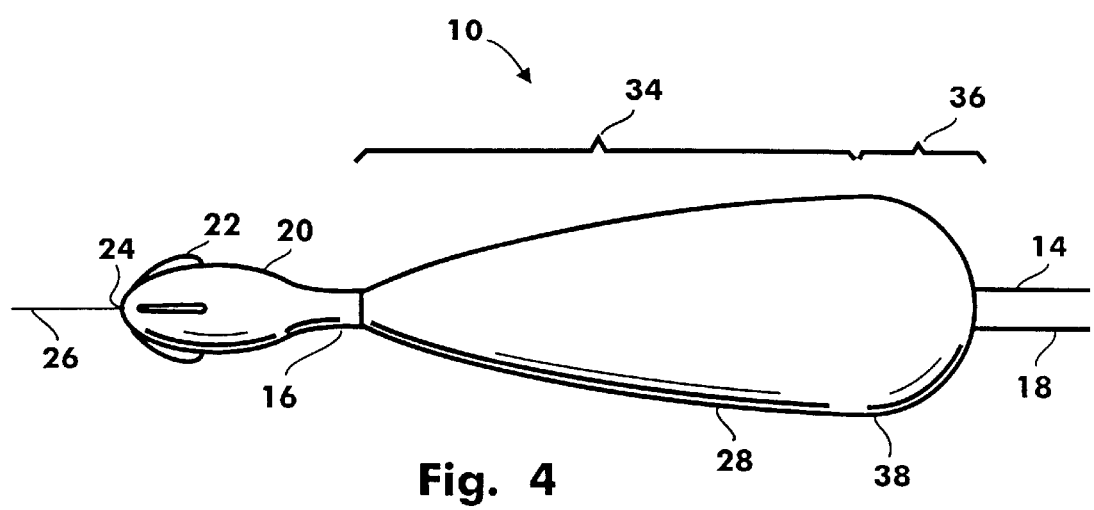
FIG. 4 is a side view of the distal portion of the present invention with the expandable balloon shown in an inflated state.

Inflation of the balloon 28 using the inflation lumen 30 may be better appreciated by reference to FIGS. 3 and 4. In FIG. 3, it may be seen that the balloon 28 is shown in an uninflated state. As a result, the balloon 28 is substantially cylindrical in shape and generally conforms to the surface of the catheter 14. In comparison, in FIG. 4, it may be seen that the balloon 28 is inflated to have a substantially fusiform shape. The fusiform shape of the inflated balloon 28 includes a tapered distal portion 34 and a tapered proximal section 36. Between the tapered distal portion 34 and tapered proximal section 36, the surface of the inflated balloon 28 rises to form an apogee 38, or point where the surface of the balloon 28 is most greatly distanced from the catheter 14. Alternatively, it may be appreciated from reference to FIG. 4, that the balloon 28 is characterized by a radius which is smallest at the distal end of the balloon 28. The radius increases over the length of the distal portion 34 of the inflatable balloon 28 and reaches a maximum value at the apogee 38. The increase in the radius, between the distal end of the balloon 28 and the apogee 38, gives the distal portion 34 of the inflatable balloon a tapered, or conical shape. In general, many different configurations are practical for the shape of the inflated balloon 28. Preferably, however, the balloon is formed so that the distal portion 34 has a more gradual taper than the proximal portion 36. It is also preferable to form the balloon 28 so that the tapering of distal portion 34 approximately corresponds to the tapering configuration of the major coronary arterial vessels.

Turning now to FIGS. 6 and 7 an alternate embodiment for the probe 20 of the present invention is shown to include a rigid shell 44 formed to surround a hollow chamber 46. The shell 44 is formed to have the same ellipsoidal shape shown for the probe 20 in FIGS. 2, 3 and 4. Shell 44, however, is formed to include a series of longitudinal slots 48 of which slot 48a and 48b are exemplary. Inside of chamber 46 a series of blades 50, of which 50a and 50b are exemplary, are mounted to a spring carrier 52. Each blade 50 is positioned to be aligned with a corresponding slot 48 formed in the shell 44. The alignment of the blades 50 and slots 48 allows the blades 50 to move from the retracted configuration of FIG. 6 where the blades 50 are fully contained within the chamber 46, to the extended configuration of FIG. 7 where each blade 50 projects from a respective slot 48.

The alternate embodiment of the present invention, shown in FIGS. 6 and 7 also includes a piston 54 and a push-pull control wire 56. The control wire 56 passes through a lumen 58 formed in the catheter 14 with the distal end of the control wire 56 positioned inside of the chamber 46. The piston 54 is mounted at the distal end of the control wire 56 and is contained within the chamber 46. The control wire 56 is free to move translationally within the catheter 14. The translational movement of the control wire 56 is accompanied, of course, by an equivalent translational movement of the piston 54. In this fashion, the proximal end of the control wire 56 (proximal end not shown) may be manipulated to cause translational movement of the piston 54 within the chamber 46.

Continuing with FIGS. 6 and 7, it may be seen that the piston 54 is formed with sloping forward shoulders 60. Functionally, distal advancement of the piston 54 caused by the control wire 56 causes the forward shoulders 60 to contract the spring carrier 52. Further distal advancement of the piston 54 forces the spring carrier 52 to separate and, as shown in FIG. 7, causes each of the blades 50 to move radially outward to project the blades 50 from the shell 44. Proximal movement of the piston 54, once again caused by the control wire 56, allows the blades 50 to once again retract into the chamber 46.

A motor 62 can be remotely attached to the catheter 14 and can be used to alternately advance or withdraw the entire probe 20 once the blades 50a and 50b are outwardly projected from the shell 44 to assist in cutting of the stenotic segment 42. Alternately, the motor can be used to alternately advance or withdraw the push-pull control wire 56, which in turn, advances or withdraws the piston 54. This action causes the blades 50 to reciprocally project from the shell 44 and withdraw into the shell 44. The frequency and amount of movement of the motor 62 and blades 50 can vary according to the stenotic segment.

OPERATION

Figure 5:
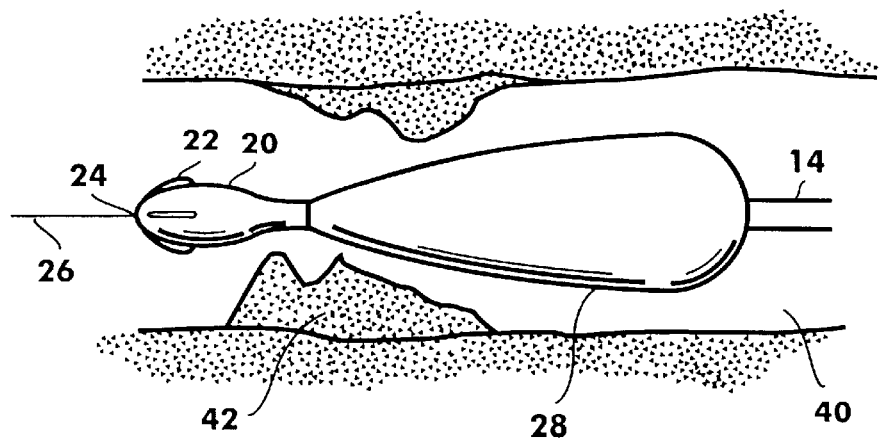
FIG. 5 is a plan view of the present invention shown operationally positioned within a vessel of a patient.

In operation of the present invention, as best seen in FIG. 5, a guidewire, such as guidewire 26 is prepositioned in the arterial system of a patient. More specifically, the guidewire 26 is advanced into a vessel 40 of the patient until the distal end of the guidewire 26 is positioned within or beyond the stenotic segment 42 that is the target of the procedure. The proximal end of the guidewire is then inserted into the guidewire lumen 24 of the probe 20 and catheter 14 and the probe 20 and catheter 14 are advanced over the guidewire 26 until the probe 20 is adjacent to the target stenosis 42.

Incision of the target stenosis 42 then proceeds by advancing the probe 20 and blades 24 through the stenosis 42. Incision of the stenotic segment 42 may be repeated by retracting and the re-advancing the probe 20 and blades 22 through the stenotic segment 42 in a reciprocal motion.

Once the stenotic segment 42 has been properly incised, fluid from a pressure source (such as the pressure source 32 of FIG. 1) may be passed under control of a controller (such as the controller 33 of FIG. 1) through the inflation lumen 30 of the catheter 14 to inflate the balloon 28. The inflating balloon 28 forcibly dilates the stenosis 42 in a manner which is somewhat similar to a typical angioplasty procedure. During the dilation process, however, the fusiform shape of the inflating balloon 28 helps the balloon 28 to conform to the tapering geometry present in vessel 40. In this fashion, the fusiform shape of the balloon 28 allows the balloon 28 to evenly apply pressure along the vessel 40, preventing overpressurization of any particular part of vessel 40.

Alternatively, the fusiform shape of the balloon 28 allows the balloon to be used as a dilation probe. The balloon 28 may be advanced to dilate the stenotic segment 42 and the inflation of the balloon 28 may be increased or decreased during the dilation process. Dilation of the stenotic segment 42 may be repeated by retracting and the re-advancing the balloon 28 through the stenotic segment 42 in a reciprocal motion.

Operationally, the use of the alternate embodiment of FIGS. 6 and 7 is similar to the operational sequence already described. When the alternate embodiment of FIGS. 6 and 7 is utilized, however, the blades 50 may be withdrawn into the chamber 46 whenever the incising ability of the blades 50 is not required. In this fashion, inadvertent contact between the blades 50 and the patient's vascular system is avoided. Additionally, it may be appreciated that the blades 50 may be extended a variable distance from the shell 44 allowing the alternate embodiment of FIGS. 6 and 7 to provide a selectable incising depth.

While the particular device for incising and dilating a stenosis within a vessel as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A device for incising and dilating stenotic tissue within a lumen of a vessel, the device comprising:
    a catheter having a distal end;
    a probe mounted on the catheter proximate the distal end, the probe having a distal portion which includes a tapered section having a proximally increasing cross-section;
    at least three blades moveable between a first configuration where the blades are retracted into the probe and a second configuration where the blades extend along the tapered section of the probe for incising the stenotic tissue and wherein a distal end of at least one of the blades is pivotably attached to the probe; and
    an inflatable balloon for dilating the stenotic tissue, the balloon being mounted proximally to the probe.

2. The device of claim 1 wherein the balloon has a distal end, a proximal end, and a surface with an apogee thereon between the distal end and the proximal end of the balloon, and the surface of the balloon between the distal end of the balloon and the apogee is tapered with a proximally increasing radius when the balloon is inflated.

3. A device as recited in claim 1 wherein the blades are spaced apart and extend substantially radially from the tapered section of the probe.

4. A device as recited in claim 1 including four spaced apart blades positioned substantially radially around the probe.

5. A device as recited in claim 1 wherein the probe is formed to surround a chamber and wherein the blades are positioned within the chamber in the first configuration.

6. The device of claim 1 including a wedge shaped piston which moves relative to the catheter and facilitates movement of at least one blade between the first configuration and the second configuration.

7. The device of claim 1 wherein the probe has an apogee with a larger diameter than an outer diameter of the catheter.

8. A device as recited in claim 1 including a spring carrier securing a distal end of one of the blades to the catheter.

9. A device for incising and dilating stenotic tissue within a lumen of a vessel, the device comprising:
    a catheter;
    a probe secured to the catheter, the probe having a distal portion, the distal portion including a tapered section having a proximally increasing cross-section; and
    a blade including a distal end which is pivotably attached to the probe and extends through the tapered section of the probe for incising the stenotic tissue.

10. The device of claim 9 including at least three blades which extend substantially radially from the probe, the blades being movable between a first configuration where the blades are retracted into the probe and a second configuration where the blades extend from the probe.

11. The device of claim 9 including an inflatable balloon secured to the catheter for selectively dilating the stenotic tissue.

12. The device of claim 11 wherein the balloon includes a distal end, a proximal end and a surface with an apogee thereon between the distal end and the proximal end of the balloon, and the surface of the balloon between the distal end of the balloon and the apogee is tapered with a proximally increasing radius when the balloon is inflated.

13. The device of claim 9 including a spring carrier securing the distal end of the blade to the catheter.

14. The device of claim 9 including a wedge shape piston which moves relative to the catheter and facilitates pivoting of the blade.

15. The device of claim 9 further comprising a motor for selectively and alternately moving the blade between a first configuration wherein the blade is retracted into the probe and a second configuration wherein the blade extends from the probe.

16. The device of claim 9 wherein the probe has an apogee with a larger diameter than an outer diameter of the catheter.

17. A method for incising, and dilating a stenotic tissue within a lumen of a vessel, the method comprising the steps of:
    providing a device which includes (i) a catheter having a distal end, (ii) a substantially rigid probe having a distal portion which includes a tapered section having a proximally increasing cross-section, (iii) at least three blades being adapted for selectively extending from the tapered section, the blades being moveable between a first configuration where the blades are retracted into the probe and a second configuration where the blades extend along the tapered section of the probe for incising the stenotic tissue and wherein a distal end of at least one of the blades ls pivotably attached to the probe, and (iv) an inflatable balloon for dilating the stenotic tissue, the balloon being mounted on the catheter proximally to the probe;
    advancing the device through the vessel to position the distal end of the device proximate the stenotic tissue;
    extending the at least three blades at least partly from the probe from the first configuration toward the second configuration;
    advancing the probe through the stenotic tissue to incise the stenotic tissue; and
    inflating the balloon to dilate the stenotic tissue.

18. A method as recited in claim 17 further comprising the steps of:
    providing a guidewire;
    positioning the guidewire in the vessel; and
    advancing the device over the guidewire.

* * * * *